US011545350B2

United States Patent
Tanaka et al.

(10) Patent No.: US 11,545,350 B2
(45) Date of Patent: Jan. 3, 2023

(54) METHOD FOR STRUCTURAL ANALYSIS OF ORGANIC COMPOUND

(71) Applicants: SHIMADZU CORPORATION, Kyoto (JP); HIROSHIMA UNIVERSITY, Higashihiroshima (JP)

(72) Inventors: Koichi Tanaka, Kyoto (JP); Takushi Yamamoto, Kyoto (JP); Manaho Yamaguchi, Higashihiroshima (JP); Shunsuke Izumi, Higashihiroshima (JP)

(73) Assignees: SHIMADZU CORPORATION, Kyoto (JP); HIROSHIMA UNIVERSITY, Higashihiroshima (JP)

( * ) Notice: Subject to any disclaimer, the term of this patent is extended or adjusted under 35 U.S.C. 154(b) by 4 days.

(21) Appl. No.: 17/237,273

(22) Filed: Jun. 28, 2021

(65) Prior Publication Data
US 2021/0358733 A1   Nov. 18, 2021

(51) Int. Cl.
| | | |
|---|---|---|
| *H01J 49/16* | (2006.01) | |
| *G01N 33/487* | (2006.01) | |
| *G01N 27/626* | (2021.01) | |
| *H01J 49/00* | (2006.01) | |
| *G01N 33/00* | (2006.01) | |
| *G01N 33/68* | (2006.01) | |

(52) U.S. Cl.
CPC .......... *H01J 49/164* (2013.01); *G01N 27/628* (2013.01); *G01N 33/0047* (2013.01); *G01N 33/487* (2013.01); *G01N 33/68* (2013.01); *H01J 49/0004* (2013.01)

(58) Field of Classification Search
CPC .. H01J 49/164; H01J 49/0004; H01J 49/0045; G01N 27/628; G01N 27/62; G01N 33/487; G01N 33/6851; G01N 33/0047; G01N 33/68

USPC ........................................................ 250/288
See application file for complete search history.

(56) References Cited

U.S. PATENT DOCUMENTS 6,558,902 B1 *   5/2003   Hillenkamp ..........   H01J 49/164
                                                     506/6

OTHER PUBLICATIONS

"iMScope TRIO Imeejingu Shitsuryo Kenbikyo (iMScope TRIO imaging mass microscope)", Shimadzu Corporation, [online], [accessed on Mar. 19, 2020], the Internet.

(Continued)

*Primary Examiner* — Kiet T Nguyen
(74) *Attorney, Agent, or Firm* — Sughrue Mion, PLLC

(57) ABSTRACT

One mode is a method for the structural analysis of an organic compound by MALDI mass spectrometry, including: a sample preparation process (S1) which includes preparing a sample by mixing a specimen containing an organic compound to be analyzed with a predetermined matrix at a mixture ratio within a range from 1:5 to 1:5000 in molar ratio; a mass spectrometry process (S3) which includes irradiating the prepared sample with a laser beam having a spot size equal to or smaller than 15 μm to generate ions originating from a component of the specimen in the sample, and performing a mass spectrometric analysis of the generated ions; and an analyzing process (S4) which includes detecting, from a mass spectrum acquired in the mass spectrometry process, ions including product ions resulting from in-source decay, and estimating the structure of the organic compound to be analyzed based on information concerning the ions.

8 Claims, 10 Drawing Sheets

(56) References Cited

OTHER PUBLICATIONS

Mariko Yamakoshi et al., "Oxidative radical driven cleavage of peptide backbone caused by matrix-assisted laser desorption/ionization-in-source decay with low matrix-to-peptide molar ratios", International Journal of Mass Spectrometry, 2017, pp. 56-61, vol. 422.

Yuko Fukuyama et al., "3-Hydroxy-2-Nitrobenzoic Acid as a MALDI Matrix for In-Source Decay and Evaluation of the Isomers", Journal of American Society for Mass Spectrometry, 2018, pp. 2227-2236, vol. 29, No. 11.

* cited by examiner

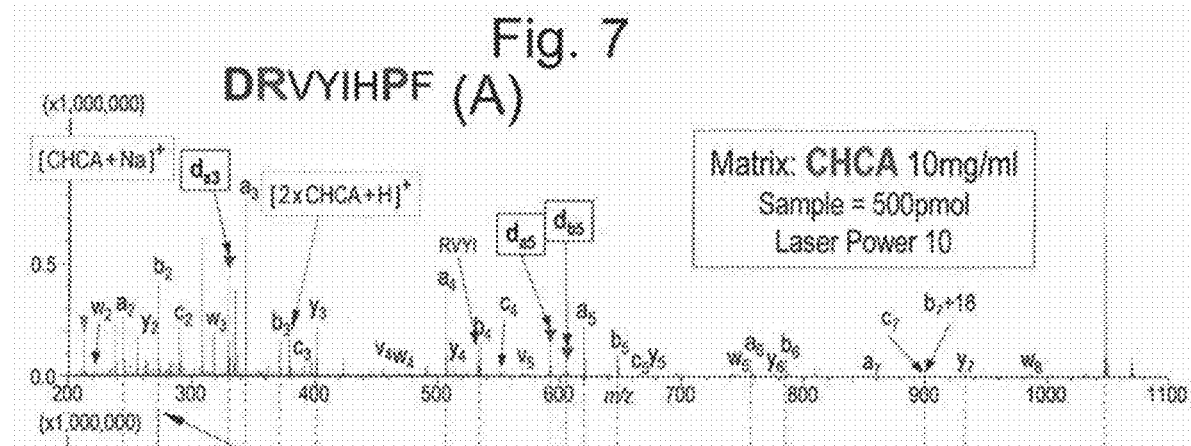
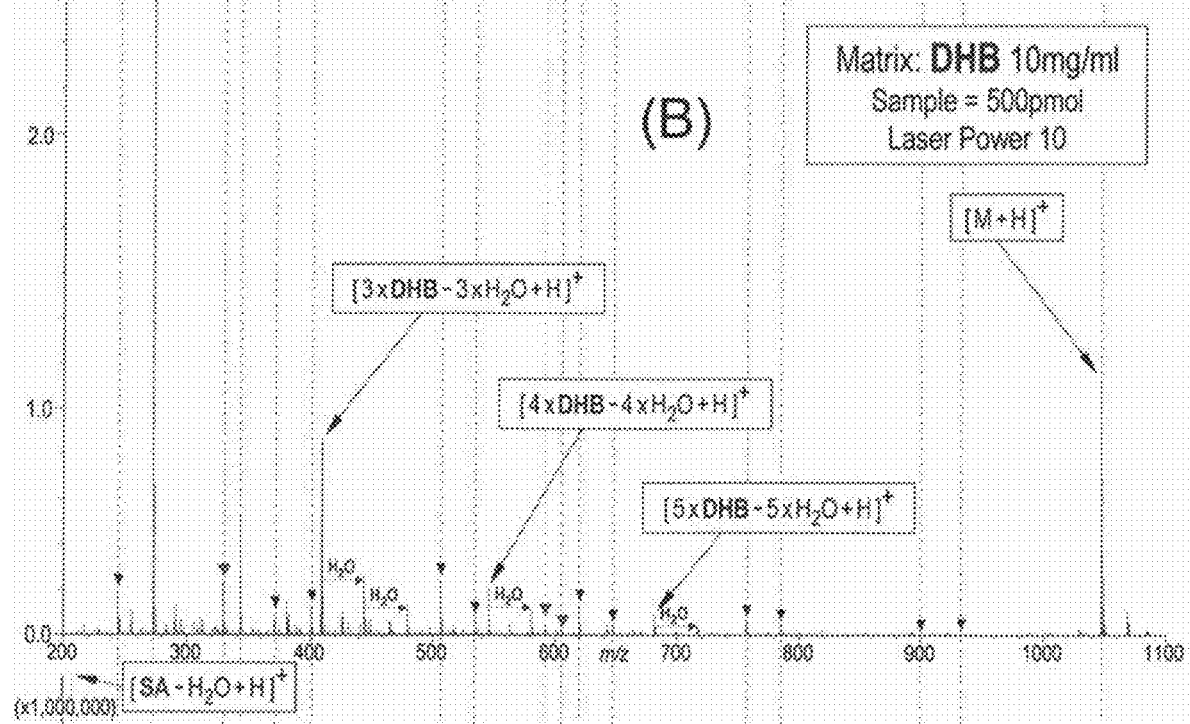
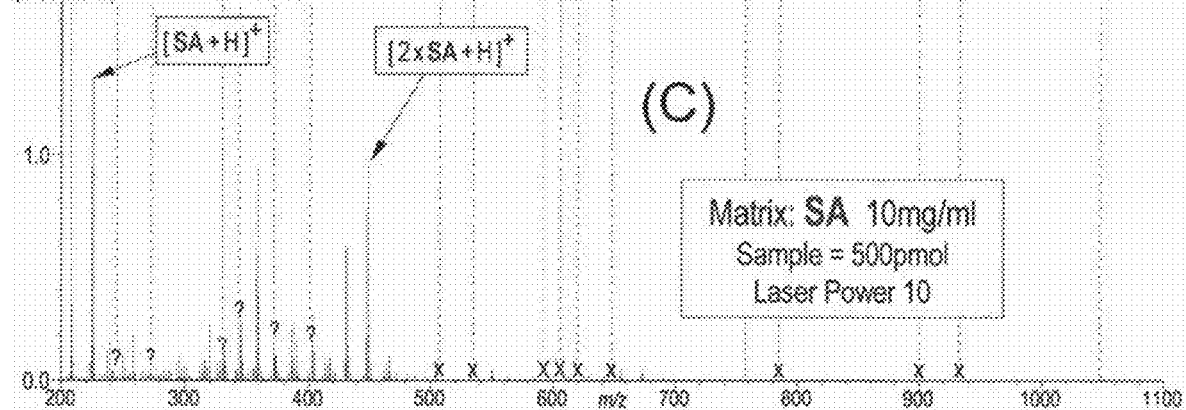
Fig. 7

Fig. 8
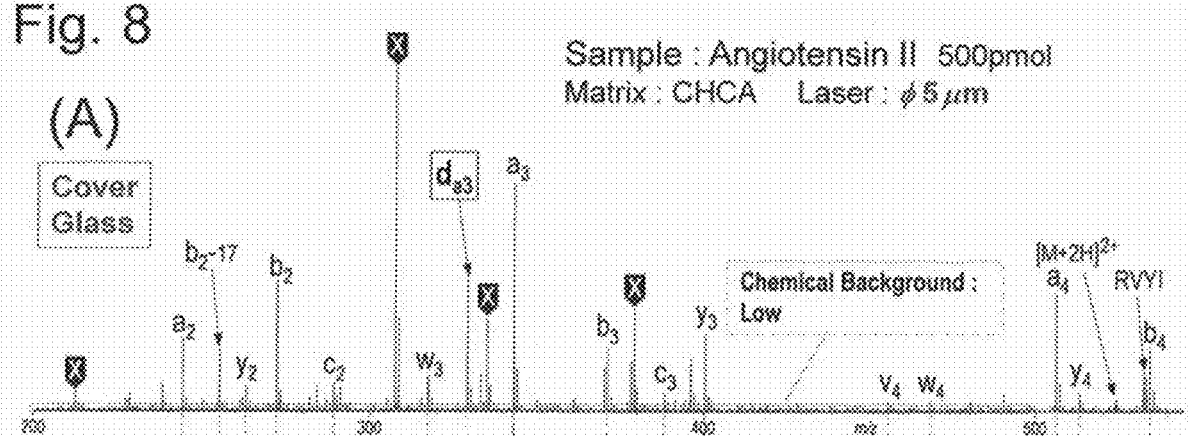
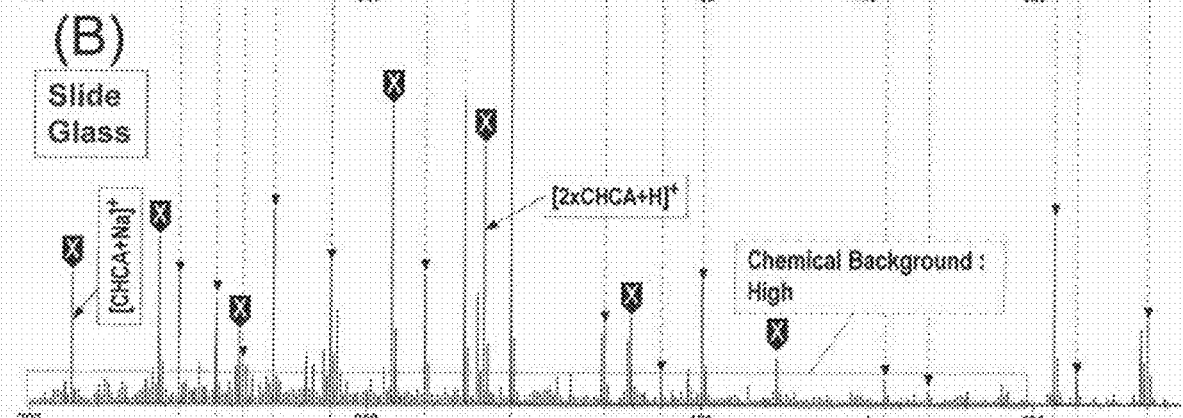
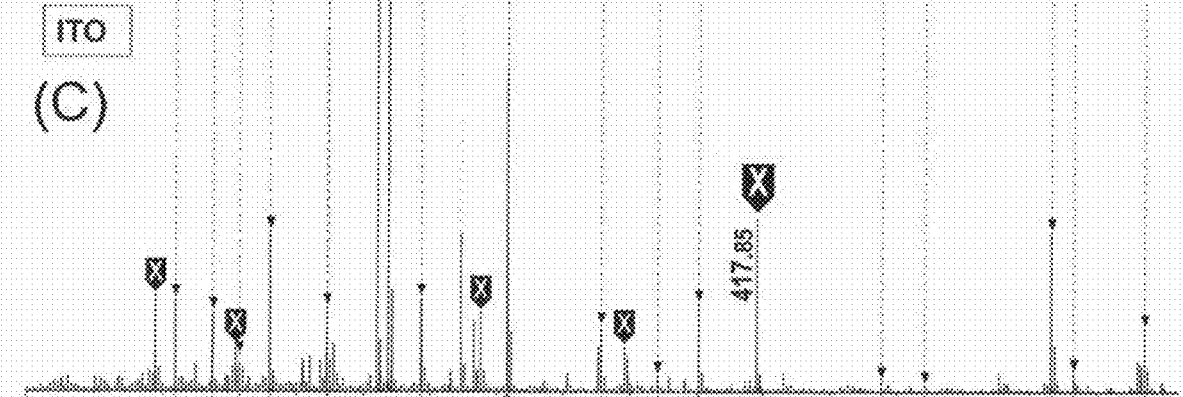
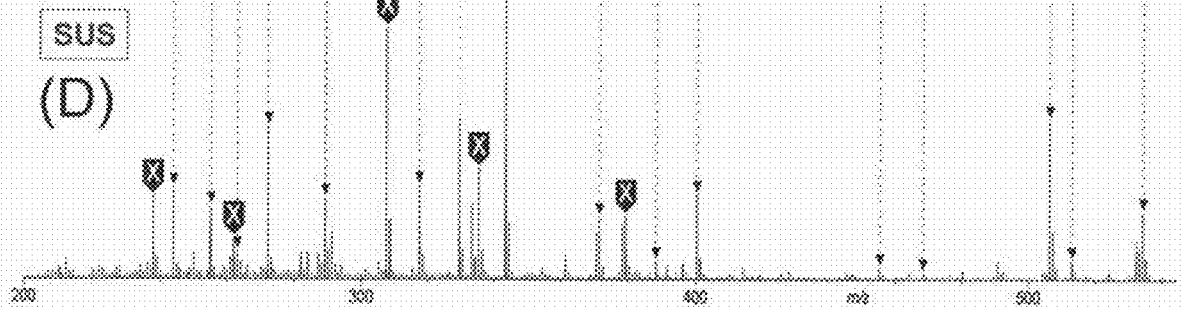

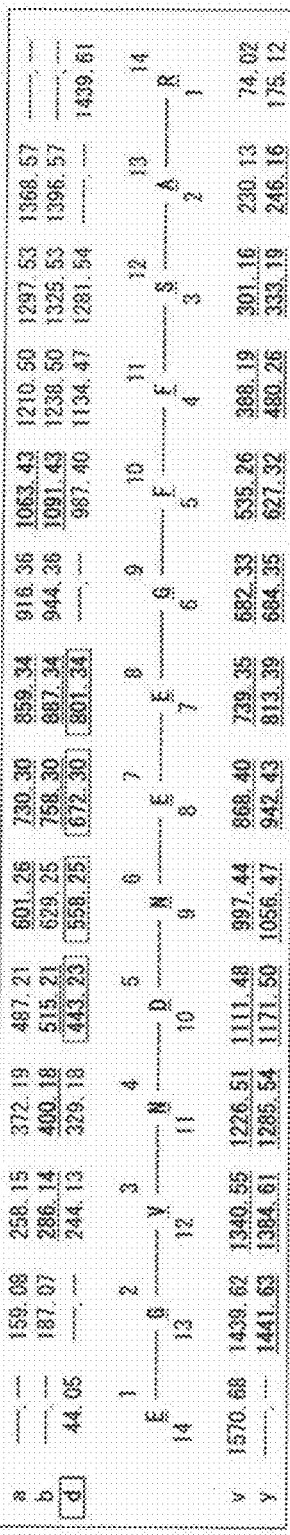
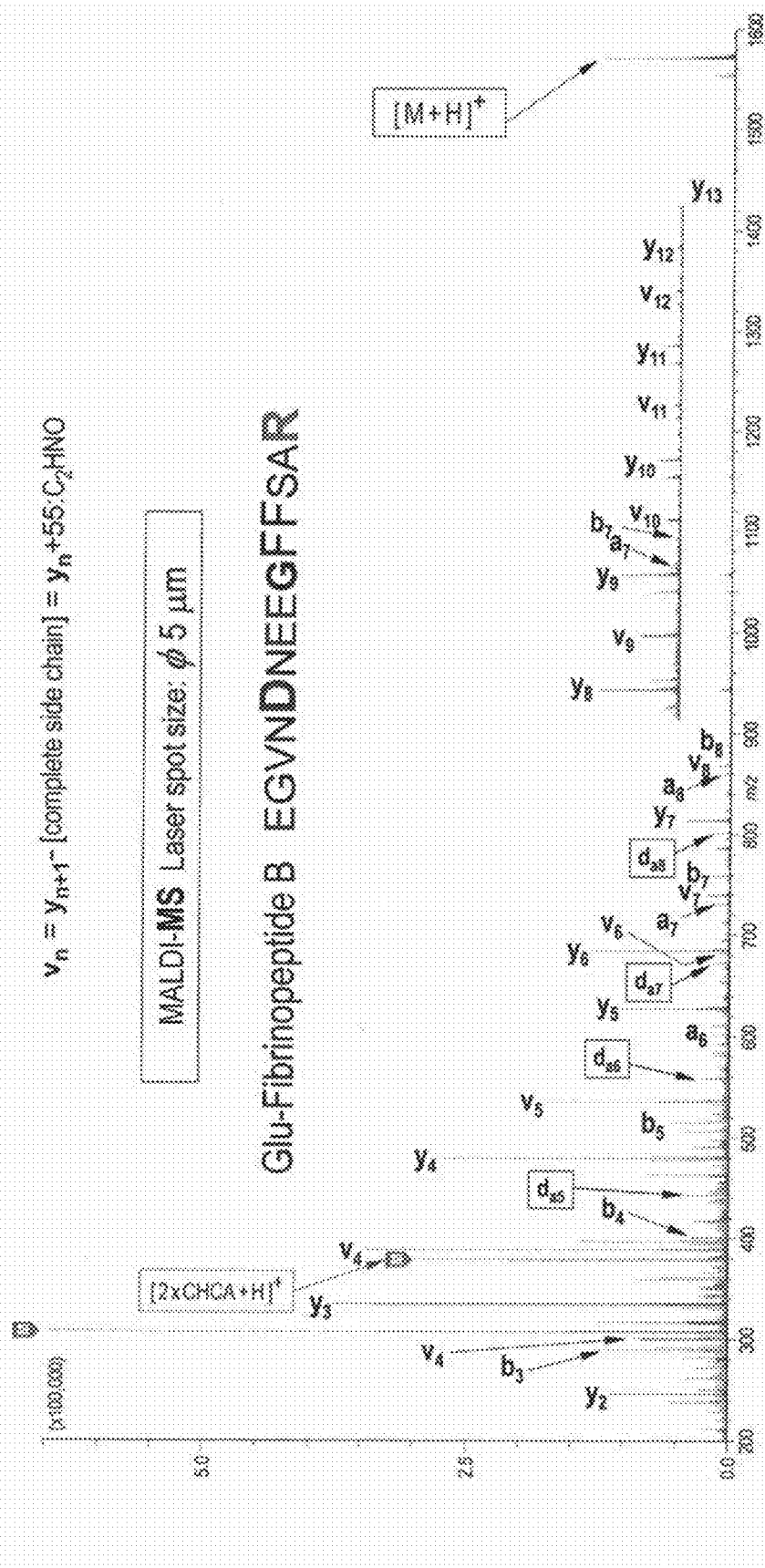
Fig. 9

METHOD FOR STRUCTURAL ANALYSIS OF ORGANIC COMPOUND

TECHNICAL FIELD

The present invention relates to a method for the structural analysis of an organic compound by mass spectrometry, and more specifically, to a method that is suited for analyzing the structure of a peptide, protein, glycan or similar compound.

BACKGROUND ART

In a mass spectrometer using an ion source which employs matrix assisted laser desorption/ionization (MALDI; this type of device is hereinafter called the "MALDI mass spectrometer"), a sample prepared by mixing a specimen to be analyzed with an ionization agent, called the "matrix", is irradiated with laser light for a short period of time to vaporize and ionize a component of the specimen in the sample. The generated ions are introduced into a mass separator, which separates the ions according to their mass-to-charge ratios and detects them.

The MALDI method is generally known as a soft ionization method which can ionize a hard-to-volatile compound without significantly fragmenting the compound. Therefore, mass spectrometers in which a MALDI ion source is coupled with a time-of-flight mass separator having a high level of mass-resolving power and mass accuracy are often used to perform a measurement of a molecular ion produced from a protein, peptide or similar compound of biological origin (e.g., a protonated molecule $[M+H]^+$, where M represents a specimen molecule which is the analysis target) and acquire its molecular weight information. In this type of measurement, since detection sensitivity is important, the spot size of the laser beam is intentionally increased (e.g., 50-200 μm in diameter) so that a considerable amount of ions will be generated by a single shot of laser irradiation.

On the other hand, in the case of analyzing the amino-acid sequence of a peptide or the structure of a glycan (or the like), it is necessary to intentionally fragment the peptide or glycan into fragments and acquire mass information of the various partial structures resulting from the fragmentation. A technique widely used for this purpose is an MS/MS analysis (or $MS^n$ analysis with n being equal to or greater than three) employing a low-energy collision induced dissociation, high-energy collision induced dissociation or other dissociation techniques.

For example, an imaging mass spectrometer disclosed in Non Patent Literature 1 includes an atmospheric pressure MALDI ion source configured to perform ionization in an ambiance of atmospheric pressure, an ion trap, and a time-of-flight mass separator. The reason why the atmospheric pressure MALDI ion source is used rather than a vacuum MALDI ion source configured to perform ionization in a vacuum atmosphere is that a biological specimen, such as a biological tissue section, should be analyzed in its natural state without being dried. As compared to the vacuum MALDI, the atmospheric pressure MALDI is normally less likely to cause the fragmentation of ions through the ionization process. Accordingly, in the aforementioned imaging mass spectrometer, when the mass information of a target compound in a biological specimen needs to be acquired, the ions derived from the target compound generated in the atmospheric pressure MALDI ion source are mass-separated and detected by the time-of-flight mass separator without being dissociated by the ion trap. On the other hand, when a structural analysis of the target compound needs to be performed, the ions derived from the target compound generated in the atmospheric pressure MALDI ion source are dissociated by low-energy CID in the ion trap, and the thereby generated product ions are mass-separated and detected by the time-of-flight mass separator.

When the target compound is a peptide, the mass spectrum acquired through this type of MS/MS analysis shows a large number of product ions resulting from the cleavage of the main chain of the peptide, such as the a-type, b-type, c-type and y-type product ions expressing the amino-acid sequence information. However, low-energy CID often leads to the observation of internal fragment ions which include neither the N-terminal nor the C-terminal, or ions resulting from the cleavage of the main chain at multiple locations (e.g., a[-17] or b[-17/18]). On the other hand, the d-type, w-type or other types of product ions, which result from the cleavage of a side chain useful for distinguishing between leucine and isoleucine which are structurally isomeric amino acids, are barely observed. Therefore, the aforementioned mass spectrum does not always contain a sufficient amount of information for a detailed structural analysis of a peptide, and the structural analysis may not be satisfactorily performed.

There is another type of technique, called in-source decay (ISD), by which a mass spectrum that allows for a structural analysis can be acquired. Regarding the ionization process by the MALDI method, it is commonly known that the dissociation of ions derived from a substance subjected to the measurement can be promoted by increasing the amount of ionization energy (e.g., by increasing the power of the laser light) or using a special kind of matrix. In-source decay utilizes this fact and enables the acquisition of a mass spectrum on which product ions are observed, without using an element for dissociating ions, such an ion trap or collision cell.

Various studies have conventionally been conducted on what form of in-source decay occurs under what conditions. For example, Non Patent Literature 2 reports that a special kind of product ion is likely to be generated by using 1,5-Diaminonaphthalene (which is hereinafter called "1,5-DAN" according to common practice) as the matrix and performing the ionization by a vacuum MALDI method under the condition that the molar ratio of the matrix mixed with the specimen is considerably lower than in the case of a normal vacuum MALDI method. However, the document does not report that d-type ions can be observed.

Non Patent Literature 3 reports that product ions including d-type ions can be obtained in a vacuum MALDI method in which 3-Hydroxy-2-nitrobenzoic acid (which is hereinafter called the "3H2NBA" according to common practice) is used as the matrix.

CITATION LIST

Non Patent Literature

Non Patent Literature 1: "iMScope TRIO Imeejingu Shitsuryo Kenbikyo (iMScope TRIO imaging mass microscope)", Shimadzu Corporation, [online], [accessed on Mar. 19, 2020], the Internet Non Patent Literature 2: Mariko Yamakoshi and another author, "Oxidative radical driven cleavage of peptide backbone caused by matrix-assisted laser desorption/ionization-in-source decay with low matrix-to-peptide molar ratios", *International Journal of Mass Spectrometry*, 2017, Vol. 422, pp. 56-61

Non Patent Literature 3: Yuko Fukuyama and two other authors, "3-Hydroxy-2-Nitrobenzoic Acid as a MALDI Matrix for In-Source Decay and Evaluation of the Isomers", *Journal of American Society for Mass Spectrometry*, 2018, Vol. 29, No. 11, pp. 2227-2236

SUMMARY OF INVENTION

Technical Problem

However, in a mass spectrum acquired through the conventional in-source decay in the previously described manner, it is often the case that various kinds of cluster ions originating from the matrix (e.g., [n×matrix+H]$^+$) are abundantly observed, obstructing the structural analysis of the peptide. Another problem is that the analysis requires a considerable amount of time, labor and cost due to the use of a special matrix other than a commonly used matrix for the MALDI method, such as α-cyano-4-hydroxycinnamic acid (CHCA) or 2,5-dihydroxybenzoic acid (DHB).

The present invention has been developed to solve at least one of those problems. Its primary objective is to acquire satisfactory information concerning product ions that are useful for analyzing a detailed structure of a peptide, glycan, or similar organic compound.

Solution to Problem

Through experimental studies on the relationship between the analysis conditions in a MALDI mass spectrometric analysis and the resulting mass spectra, the present inventors have discovered the fact that various product ions which are useful for a structural analysis of a peptide can be abundantly observed by using an imaging mass spectrometer disclosed in Non Patent Literature for a mass spectrometric analysis of a sample prepared under specific conditions. Further intensive experiments have led to the finding that the primary reason why those product ions can be observed is that the imaging mass spectrometer can considerably decrease the spot size of the laser beam delivered onto a sample, since it is essential to achieve a high level of spatial resolving power. Based on those findings, the present inventors have conceived the present invention.

Thus, one mode of the present invention developed for solving one of the previously described problems is a method for the structural analysis of an organic compound by matrix assisted laser desorption/ionization mass spectrometry, the method including:

a sample preparation process which includes preparing a sample by mixing a specimen containing an organic compound to be analyzed with a predetermined matrix at a mixture ratio within a range from 1:5 to 1:5000 in molar ratio;

a mass spectrometry process which includes irradiating the prepared sample with a laser beam having a spot size equal to or smaller than 15 μm to generate ions originating from a component of the specimen in the sample, and performing a mass spectrometric analysis of the generated ions; and an analyzing process which includes detecting, from a mass spectrum acquired in the mass spectrometry process, ions including product ions resulting from in-source decay, and estimating the structure of the organic compound to be analyzed based on information concerning the ions.

Examples of the "organic compound to be analyzed" in the present invention include peptides, proteins, lipids and nucleic-acid-related substances.

Advantageous Effects of Invention

In a MALDI mass spectrometric analysis whose main objective is to acquire molecular weight information of a compound, normally, the mixture ratio of the specimen containing a compound to be analyzed to the matrix is, for example, 1:100000 or even larger in molar ratio. By comparison, in the present invention, the proportion of the specimen to be mixed with the matrix is dramatically larger. Additionally, in a MALDI mass spectrometric analysis whose main objective is to acquire molecular weight information of a compound, it is often the case that the spot size of the laser beam is, for example, within a range from 50 to 200 μm, as noted earlier. As compared to that, the laser spot size in the present invention is dramatically smaller and comparable to the size used in a device configured to perform an imaging mass spectrometric analysis with a high level of spatial resolving power.

Thus, according to the present invention, the ionization by MALDI is performed under unique conditions that are not used in conventional and common types of MALDI mass spectrometry, so as to cause in-source decay in which, for example, a peptide will undergo cleavage not only in the main chain but also in a side chain, thereby generating various product ions which are useful for structural analysis.

According to the present invention, a mass spectrum on which useful product ions for a detailed structural analysis of a peptide, glycan, or similar organic compound are satisfactorily observed can be obtained without performing an MS/MS analysis using low-energy CID (or the like). More specifically, a mass spectrum can be obtained on which product ions can be observed over a mass-to-charge-ratio range from roughly m/z 200 to a maximum of several thousands (normally, the upper limit is 2000 to 3000, although it depends on the type of mass spectrometer or other factors). Thus, even without a device capable of an MS/MS analysis, a structural analysis of an organic compound can be performed with a less expensive mass spectrometer. The time and labor for performing an MS/MS analysis can be omitted, so that a detailed structure of the organic compound can be efficiently understood with a high level of accuracy. Furthermore, both the molecular weight measurement and the structural analysis for the same organic compound can be performed by changing the spot size of the laser beam in the same device. This also helps improve the efficiency of the analysis of an organic compound.

BRIEF DESCRIPTION OF DRAWINGS

FIGS. 7A-7C show an example of the comparison of actual mass spectra acquired by using different kinds of matrices.

FIGS. 8A-8D show an example of the comparison of actual mass spectra acquired by using different kinds of sample plates.

FIG. 9 shows an example of the actual mass spectrum in the case where the sample was Glu-Fibrinopeptide B.

DESCRIPTION OF EMBODIMENTS

An embodiment of the method for the structural analysis of an organic compound according to the present invention is hereinafter described with reference to the drawings. The present method for structural analysis is a method for estimating the chemical structure of an organic compound to be analyzed, based on mass spectra acquired through a mass spectrometric analysis of the organic compound.

Figure 1:
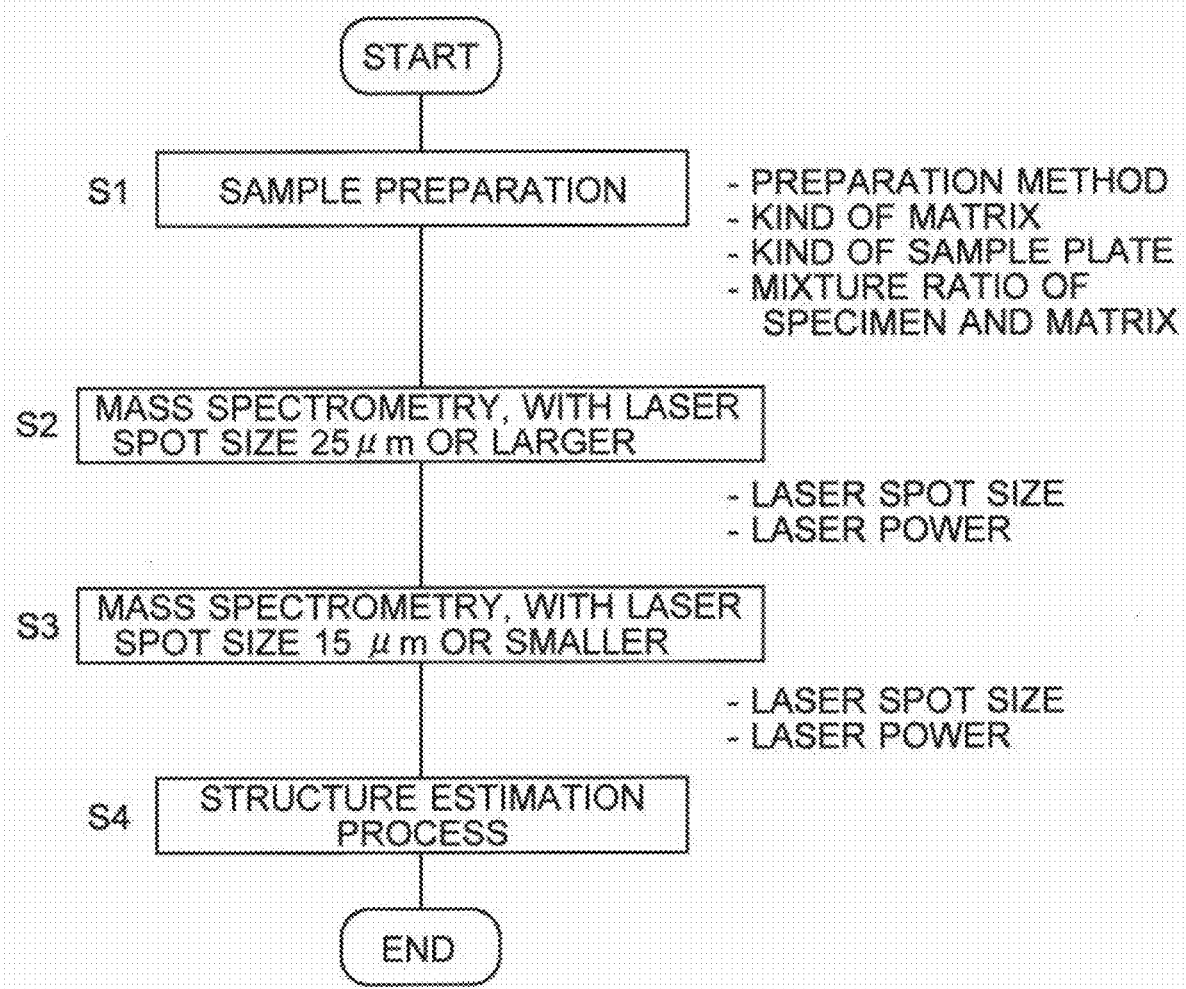
FIG. 1 is a flowchart showing the working steps of a method for the structural analysis of an organic compound according to the present invention.
Figure 2:
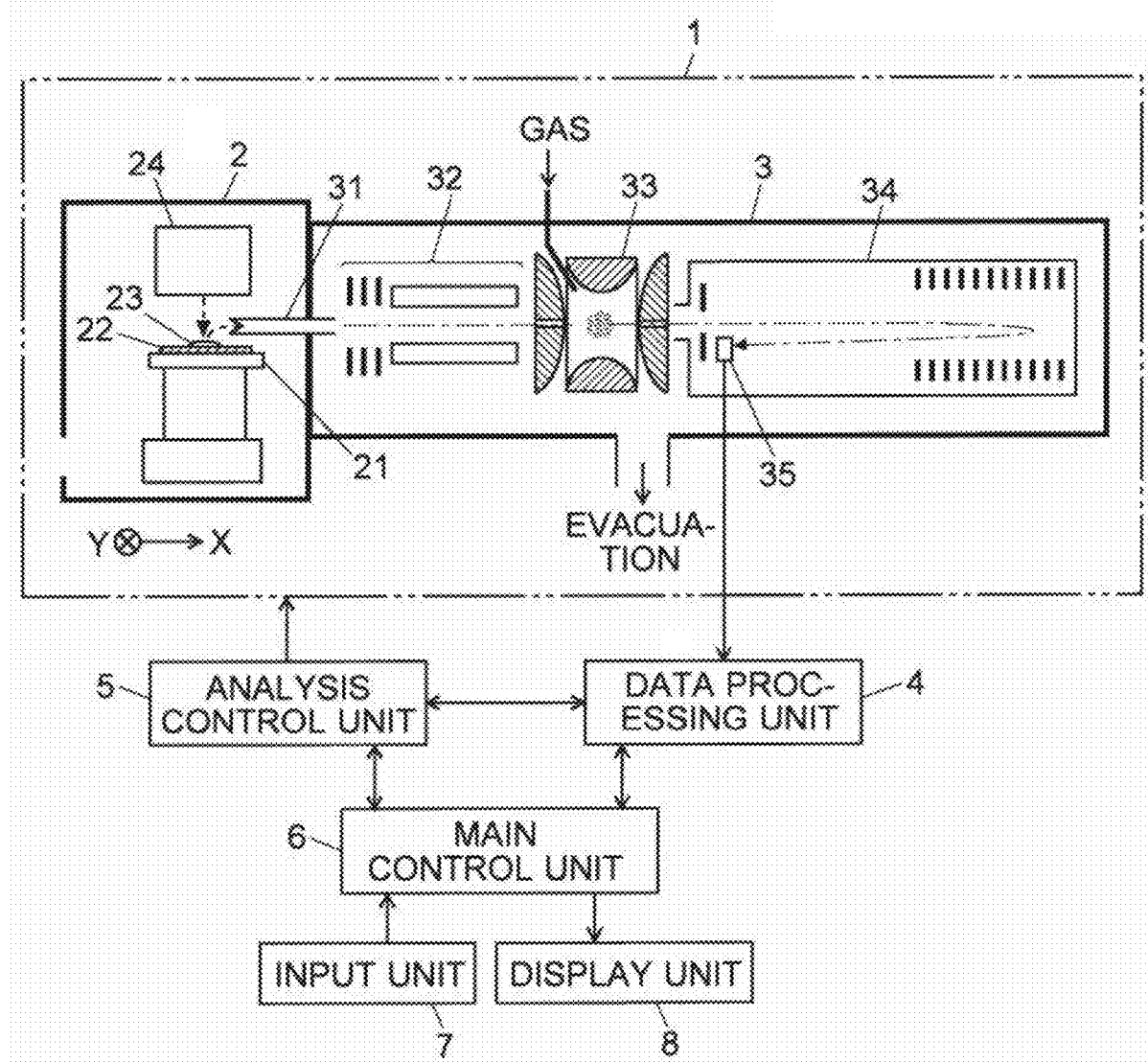
FIG. 2 is a schematic configuration diagram showing one embodiment of a mass spectrometry system for carrying out the method for the structural analysis of an organic compound according to the present invention.
Figure 3:
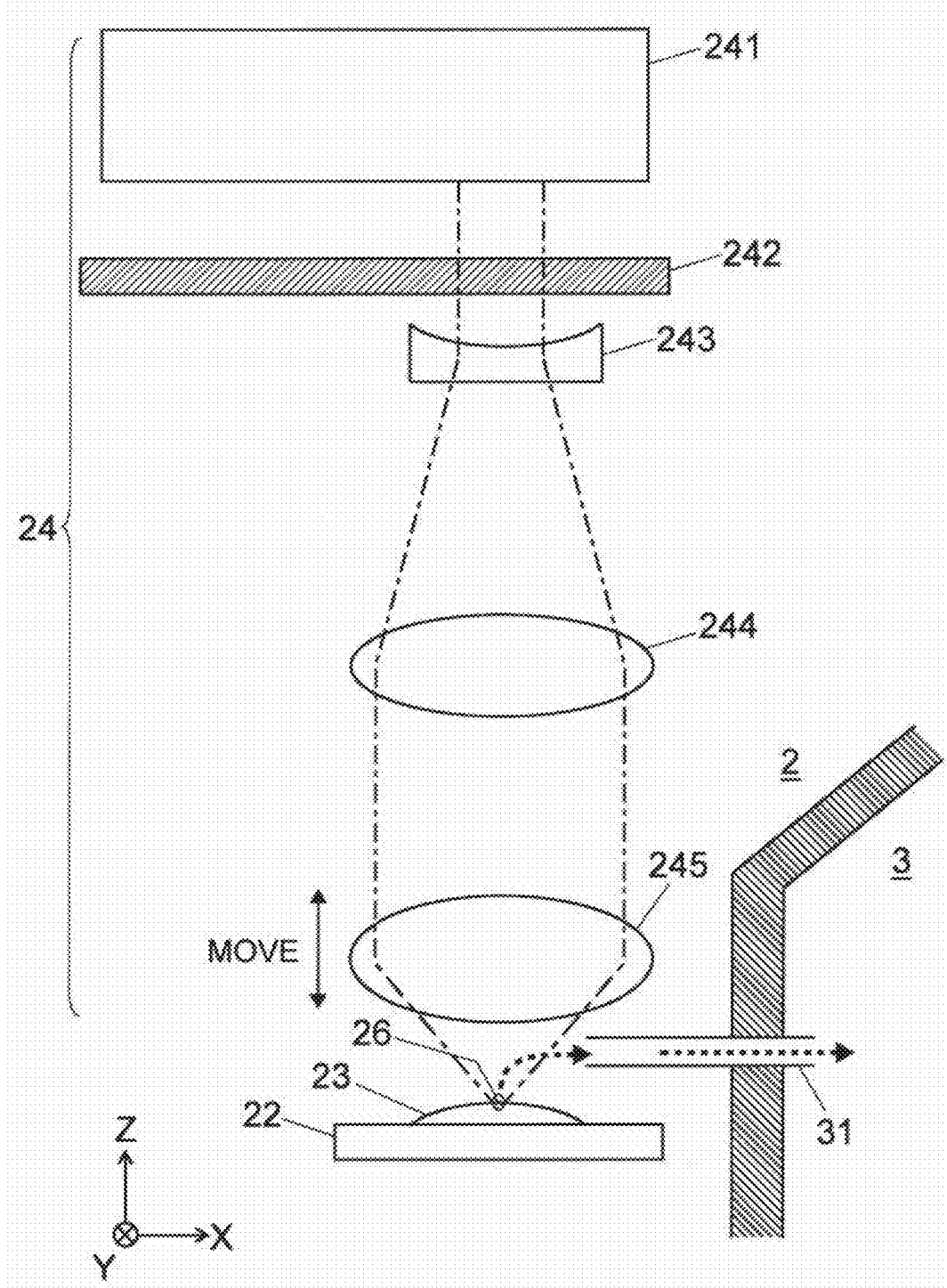
FIG. 3 is a detailed configuration diagram of the ion source in the mass spectrometry system shown in FIG. 2.

FIG. 1 is a flowchart showing the working steps of a method for the structural analysis of an organic compound according to the present invention. FIG. 2 is a schematic configuration diagram showing one example of a mass spectrometry system to be used for carrying out the method for the structural analysis of an organic compound according to the present invention. FIG. 3 is a detailed configuration diagram of the ion source in the mass spectrometry system shown in FIG. 2.

[Outline of Method for Structural Analysis of Peptide]

As one example, it is hereinafter assumed that the organic compound to be analyzed is a peptide. Peptides include both a peptide extracted from a living organism and one artificially synthesized. In the case of estimating the structure of an unknown peptide, it is necessary to collect not only information concerning various product ions generated by the cleavage of the main chain (a-type, b-type, c-type, x-type, y-type z-type and other types of ions) but also information concerning various product ions generated by the cleavage of side chains (d-type, v-type, w-type and other types of ions).

As shown in FIG. 1, for a structural analysis of a target peptide, a user initially prepares a sample to be analyzed, using a specimen containing the target peptide and a matrix for MALDI (Step S1). The user can employ an extremely common sample preparation method, such as a dried-droplet method or thin-layer method, to form the sample in a well on a prepared sample plate.

Next, using a mass spectrometry system as shown in FIG. 2, a normal mass spectrometric analysis on a sample containing the peptide is performed under predetermined analysis conditions. More specifically, an ionization with the laser spot size being equal to or larger than 25 μm, for example, is performed to mainly generate protonated molecules [M+H]$^+$, and a mass spectrometric analysis with no dissociation of the ions is subsequently performed (Step S2) to acquire a mass spectrum covering a predetermined mass-to-charge-ratio range. For the same sample, another mass spectrometric analysis in which the laser spot size for the ionization is set to be equal to or smaller than 15 μm, for example, is performed to acquire a mass spectrum covering a predetermined mass-to-charge-ratio range (Step S3).

The ionization method in the mass spectrometric analysis performed in Step S3 is a MALDI method intended for inducing the in-source decay of a protonated molecule originating from the peptide contained in the sample. A variety of product ions generated through the ionization will be observed on the mass spectrum. In other words, the mass spectrum acquired in Step S3 is effectively a mass spectrum which includes many product ions.

The molecular weight of a peptide is normally within a range from a little less than 1000 to several thousands. Therefore, important product ions are observed within a mass-to-charge-ratio range from approximately m/z 200 to a maximum of several thousands on the mass spectrum acquired in Step S3. Based on the information concerning the various ions in the mass spectrum, the process of estimating the structure of the target peptide is performed (Step S4).

The previously described sequence of the steps is quite common. Important sample preparation conditions and ionization conditions are shown on the right side of Steps S1 to S3 in FIG. 1. The sample preparation conditions include at least one of the following: the sample preparation method, kind of used matrix, kind (material) of used sample plate, mixture ratio of the specimen and the matrix, as well as other related conditions. The ionization conditions in the mass spectrometric analysis include at least one of the following: laser spot size, laser power and other related conditions. Those conditions will be described later in detail.

As will be understood from actual examples (which will be described later), it is often the case that a peak originating from a protonated molecule is also observed on the mass spectrum acquired in Step S3. Therefore, the molecular weight can be determined from that peak. In that case, the processing in Step S2 may possibly be omitted. However, it is preferable to determine the molecular weight from the mass spectrum acquired in Step S2 in the case where the protonated molecule has a large mass-to-charge ratio (which exceeds the mass-to-charge-ratio range of the mass spectrum acquired in Step S3) or its detection sensitivity is low.

[Mass Spectrometry System to be Used]

The mass spectrometry system shown in FIG. 2 is hereinafter described. This system includes a measurement unit 1, data processing unit 4, analysis control unit 5, main control unit 6, input unit 7 and display unit 8. This is substantially identical to the imaging mass spectrometer described in Non Patent Literature 1. The measurement unit 1 is an atmospheric pressure MALDI ion trap time-of-flight mass spectrometer.

In normal cases, the data processing unit 4, analysis control unit 5 and main control unit 6 are configured on a personal computer, more sophisticated workstation or similar device as a hardware resource, with their respective functions realized by executing, on the computer, dedicated control-and-processing software installed on the same computer.

The measurement unit 1 includes an ionization chamber 2 with its inner space maintained at substantially atmospheric pressure, and a vacuum chamber 3 evacuated by a vacuum pump (not shown). The ionization chamber 2 contains a sample stage 21 and a laser irradiator 24. A sample plate 22, on which a sample 23 containing a specimen to be analyzed is formed, is to be placed on the sample stage 21. The ionization chamber 2 and the vacuum chamber 3 communicate with each other through a thin ion-transport tube 31. The vacuum chamber 3 contains an ion guide 32, ion trap 33, time-of-flight mass separator 34 and ion detector 35.

Although the vacuum chamber 3 in FIG. 1 is not divided into compartments, it may be configured in the form of a multi-stage differential pumping system with the degree of vacuum successively increased from the ionization chamber 2 so that the time-of-flight mass separator 34 is under a high degree of vacuum.

As shown in FIG. 3, the laser irradiator 24 includes an ultraviolet pulse laser source 241, a variable optical filter 242, first and third lenses 243 and 244 forming a beam expander, as well as an objective lens 245. The position of the objective lens 245 can be changed by a moving mechanism (not shown) within a predetermined range in the Z-axis direction (the direction of the optical axis) in FIG. 3. This objective lens 245 is a short focus lens with a focal length of approximately 20-100 mm.

A mass spectrometric operation in the present mass spectrometry system is hereinafter schematically described.

As shown in FIG. 2, the sample plate 22 carrying the sample 23 prepared in Step S1 is set on the sample stage 21. When a command to initiate the analysis is entered through the input unit 7 by the user, the ultraviolet pulse laser source 241 under the control of the analysis control unit 5 emits a pulsed laser beam. In normal cases, the laser beam has a half-value width equal to or less than 10 nsec. The diameter of the emitted laser beam is equal to or less than 1 mm, for example. The power of this laser beam is adjusted when the beam passes through the variable optical filter 242.

After passing through the variable optical filter 242, the laser beam is temporarily expanded to, for example, a diameter of approximately 10 mm by the first lens 243 in the beam expander. The laser beam is subsequently collimated by the second lens 244 in the same beam expander. The resulting parallel beam is converged by the objective lens 245, to be delivered onto an extremely small area on the surface of the sample 23 on the sample plate 22. The laser spot size on the sample 23 depends on the position of the objective lens 245 in the Z-direction. For example, the smallest laser spot size is 15 µm or smaller, and more preferably, it should be approximately 5 µm or even smaller. The reason why such a reduction in laser spot size on the sample 23 is possible is that the short-focus objective lens 245 can be positioned close to the sample 23, which is primarily due to the use of the atmospheric pressure MALDI method.

In a time-of-flight mass spectrometer using a common type of vacuum MALDI ion source (this mass spectrometer is hereinafter called the "MALDI-TOFMS"), the ions resulting from laser irradiation are immediately extracted and accelerated from an area near the sample, to be introduced into the time-of-flight mass separator. This requires an ion extraction electrode and acceleration electrode located near the sample, making it difficult for the objective lens for laser irradiation to be positioned close to the sample. Therefore, a long-focus objective lens having a focal length of 200-300 mm, for example, is normally used, so that it is difficult to reduce the laser spot size on the sample to an extremely small diameter. Furthermore, in the first place, it is often the case with the normal MALDI-TOFMS that the laser spot size is intentionally set to be large in order to increase the amount of ions generated from the sample irradiated with one shot of laser beam and thereby improve detection sensitivity. Due to those reasons, in normal cases, the laser spot size is set within a range from approximately 50 to 200 µm.

By comparison, in the case of an imaging mass spectrometer as described in Non Patent Literature 1, the atmospheric pressure MALDI method is used as the ionization method to allow an analysis of a biological tissue section or similar type of specimen, and the generated ions are suctioned through a thin capillary tube and transported to the subsequent stage. Therefore, the objective lens can be positioned close to the sample, as shown in FIG. 3. Additionally, since imaging mass spectrometers are a type of device for determining the intensity distribution of an ion having a predetermined mass-to-charge ratio within a two-dimensional area on a sample, it is essential to reduce the spot size of the laser beam on the sample in order to improve the spatial resolution of the intensity distribution. Therefore, as shown in FIG. 3, a system capable of converging the laser beam to an extremely small spot size of approximately 5 µm is adopted. With the measurement unit 1 configured in this manner, it is possible to realize an extremely small spot size of laser beam which cannot be realized with a common type of MALDI-TOFMS.

It is inferred that irradiating the sample 23 with an extremely small spot of laser beam in the previously described manner causes in-source decay by the following mechanism.

When the sample 23 is irradiated with an extremely small spot of laser beam, a wide variety of fine particles are ejected or vaporized from the sample 23, and a plume 26 in which those fine particles are mixed with gas molecules is formed in the vicinity of the surface of the sample 23. Due to the small spot size of the laser beam, the plume 26 is also small in size, but instead, has a high concentration (i.e., high density). Since the period of time of the irradiation with the laser beam is equal to or shorter than 10 nsec, the temporal change in particle density of the plume 26 is extremely rapid. That is to say, the particle density and temperature of the plume 26 in the vicinity of the surface of the sample 23 change extremely in both the temporal and spatial dimensions. Therefore, various energetic chemical reactions easily occur in the plume 26, where the in-source decay easily takes place, producing various ions through the cleavage of not only the main chain but also a side chain of the amino acids forming the peptide. This is the likely mechanism by which a wide variety of product ions comparable to those generated by irradiation with a laser beam having a large spot size are derived from the target peptide.

It should be noted that performing the ionization not in a vacuum atmosphere but in the ambiance of atmospheric pressure has a certain effect of suppressing the diffusion of the particles ablated by the irradiation with the laser beam. This fact is probably a secondary cause of the small size of the plume 26.

In FIG. 3, the left end of the ion transport tube 31 is open to the ambiance of substantially atmospheric pressure, while the right end is open to vacuum atmosphere. Due to the significant difference in pressure between the two openings, a gas flow is formed from the ionization chamber 2 into the vacuum chamber 3 through the ion transport tube 31. The various ions generated from the sample 23 in the previously described manner are suctioned into the ion transport tube 31 by this gas flow and carried into the vacuum chamber 3. Those ions are introduced through the ion guide 32 into the inner space of the ion trap 33 and temporarily accumulated within the ion trap 33. Subsequently, the accumulated ions are simultaneously released from the ion trap 33 at a predetermined timing and introduced into the time-of-flight mass separator 34. In the time-of-flight mass separator 34, the ions are separated from each other according to their mass-to-charge ratios and reach the ion detector 35. The ion detector 35 produces a detection signal having an intensity corresponding to the amount of incident ions.

The data processing unit 4 receives the detection signals produced by the ion detector 35, converts those signals into digital data, and converts, into mass to charge ratios, the times of flight as measured from the point in time of the ejection of the ions, to create a mass spectrum showing the relationship between the mass-to-charge ratios and intensities of the ions. The mass spectrum is displayed on the screen of the display unit 8 via the main control unit 6. Furthermore, in the data processing unit 4, information concerning the product ions which are most likely to have originated from the target peptide is extracted from the created mass spectrum, and a structure including the amino-acid sequence of the target peptide is estimated from the mass-to-charge ratios and intensities of the extracted product ions.

As noted earlier, a wide variety of product ions originating from the target peptide are generated due to the in-source decay in the ionization process. Accordingly, many of those product ions are observed on the mass spectrum. Particularly important are the b-type and y-type ions resulting from the cleavage of the main chain as well as the d-type and w-type ions resulting from the cleavage of a side chain. Those ions enable the estimation of the amino-acid sequence of the peptide with a high level of accuracy, as well as the distinction between leucine and isoleucine which cannot be simply distinguished by their masses. The amount of generation of the cluster ions which normally tend to occur within a mass-to-charge-ratio from approximately m/z 200 to a maximum of several thousands due to the matrix particles added together can be reduced by preparing the sample under specific conditions (which will be described later). If a considerable number of cluster ions originating from the matrix appear with a high level of intensity on the mass spectrum, the accuracy of the structural analysis of the peptide will be significantly lowered due to those ions. Reducing those background ions improves the accuracy of the structural analysis of the peptide.

The previously described mass spectrometry system has the advantage that both the molecular weight information and structural information of the target peptide can be acquired for the same mixture of matrix and specimen by simply performing a mass spectrometric analysis with the laser spot size switched from a size equal to or larger than 25 μm to a size equal to or smaller than 15 μm.

[Conditions for Sample Preparation and Ionization]

Hereinafter described in detail are appropriate conditions for the sample preparation and ionization in the method for structural analysis according to the present embodiment, including descriptions of the results of actual measurements.

Figure 10:
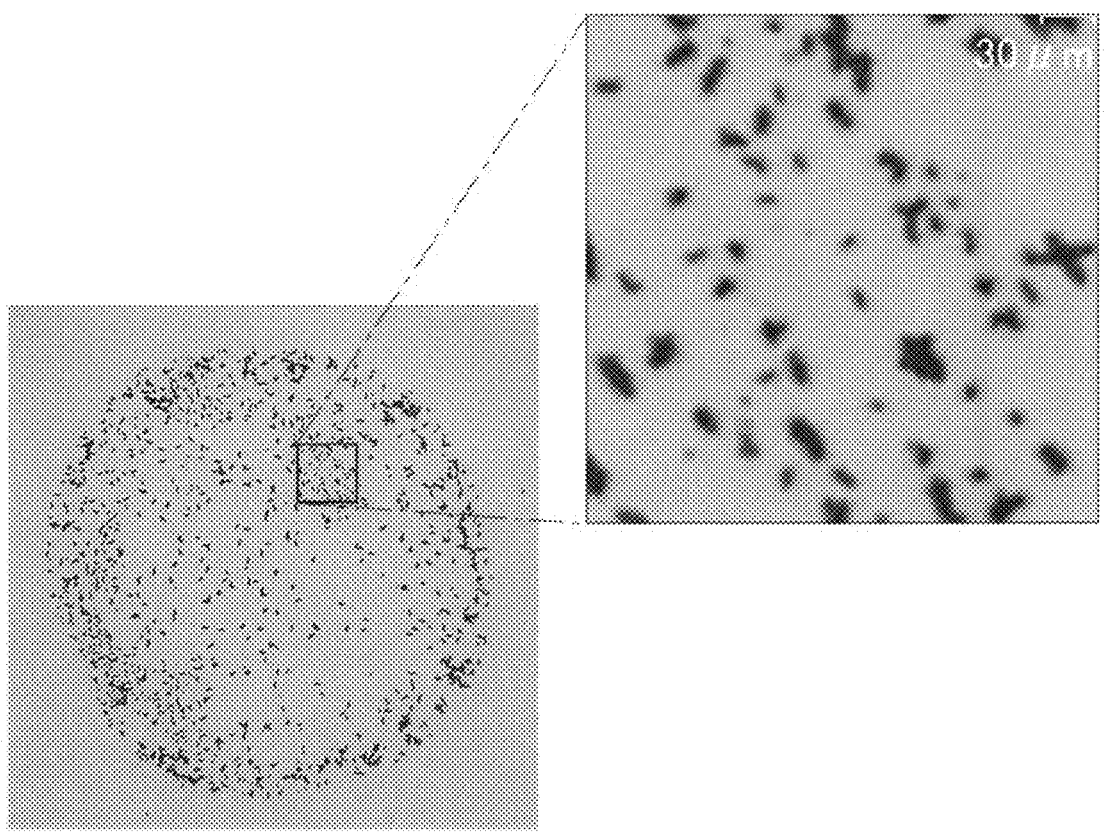
FIG. 10 shows an example of the crystal photograph of a sample.

FIGS. 4A-9 all show actual mass spectra acquired with a real device. FIG. 10 shows one example of the crystal photograph of a sample. The used mass spectrometry system was iMScope TRIO, a product manufactured by Shimadzu Corporation and disclosed in Non Patent Literature 1.

<Sample Preparation Method>

As noted earlier, a standard method can be used for the preparation of a sample, such as a dried-droplet method or thin-layer method, both of which are commonly used for vacuum MALDI. That is, the present sample preparation method is a method for preparing a sample by dropping a solution which contains at least a specimen and a matrix onto a sample plate, or by alternately dropping a solution which contains at least a specimen and a solution which contains at least a matrix onto a sample plate. The volume of the solution to be dropped is preferably equal to or larger than 0.5 μL. On the surface of the sample prepared in this manner, a considerable number of crystal grains with uneven sizes of approximately equal to or smaller than 10 μm will be observed, as shown in FIG. 10.

<Laser Spot Size>

Figure 4:
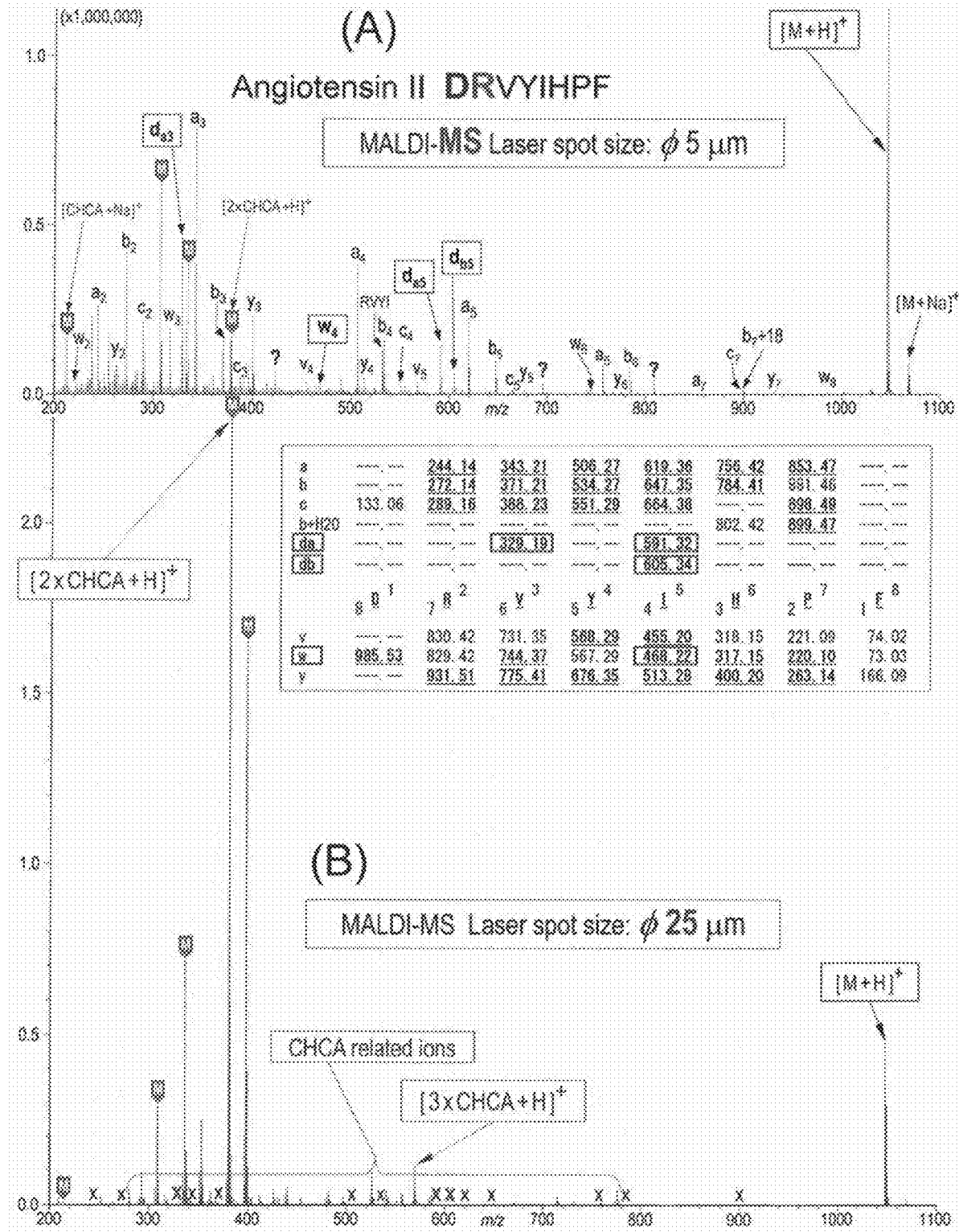
FIGS. 4A and 4B show an example of the comparison between an actual mass spectrum acquired with a laser spot size of 5 μm and one acquired with a laser spot size of 25 μm.

FIG. 4 at (A) is an actual mass spectrum acquired with a laser spot size (which is one of the ionization conditions) of 5 μm. FIG. 4 at (B) is an actual mass spectrum acquired with a laser spot size of 25 μm. FIG. 4 at (A) and (B) also includes a table showing the mass-to-charge ratios of various types of product ions which respectively correspond to the amino acids forming the target peptide, among which the ions detected on the mass spectrum shown in FIG. 4 at (A) are indicated by underlines and rectangular frames (ions with neither the underline nor rectangular frame are ions which were not detected, or ions whose peaks were practically indiscernible). The laser spot size was adjusted by changing, in the same device, the position in the Z-axis direction of the objective lens 245 shown in FIG. 3. It should be noted that the aforementioned laser spot size, 5 μm and 25 μm, are not exact values obtained by direct measurements, but are specification values selectable in the device (i.e., design values).

Other important analysis conditions were as follows:
Specimen (Peptide): angiotensin II
Matrix: CHCA
Mixture ratio of matrix and specimen: approximately 50:1 (in molar ratio)
Sample plate: cover glass for microscope As shown in FIG. 4 at (A) and the table below it, both the a-, b-, c- and y-types of ions and the d-, v- and w-types of ions originating from angiotensin II were abundantly observed when the laser spot size was 5 μm. Although some cluster ions originating from the matrix were also observed within a range of m/z 400 or smaller, the number of those ions was small, and their signal intensities were not considerably high. Furthermore, the cluster ions were barely observed within the mass-to-charge-ratio range of m/z 400 or larger, where many product ions originating from angiotensin II were observed. From these facts, it is easy to understand that the product-ion information obtained from this mass spectrum is extremely useful for the structural analysis of the peptide.

By comparison, when the laser spot size was increased to 25 μm, the observed ion species dramatically changed, as shown in FIG. 4 at (B). Ions related to the structure of angiotensin II were barely observed, while various cluster ions originating from the matrix were abundantly observed. Accordingly, it is practically impossible to perform the structural analysis of the peptide based on this mass spectrum. However, the protonated molecule $[M+H]^+$ of angiotensin II is clearly observable, and there are no other peaks around the peak, so that the peak of the protonated molecule can be easily identified. Therefore, the molecular weight of the peptide can be easily determined by using this mass spectrum.

Thus, although increasing the laser spot size to 25 μm leads to the loss of the product-ion information that is useful for the structural analysis, it facilitates the detection of the peak of the protonated molecule of the peptide. Accordingly, both the structural information and molecular weight information of the target peptide can be obtained, for example, by changing the position of the objective lens in the ion source configured as shown in FIG. 3 to switch the laser spot size between 5 μm and 25 μm.

It is inferred that increasing the laser spot size from 5 μm to 25 μm gradually decreases the product ions of peptide origin while gradually increasing the cluster ions originating from the matrix. Although the situation is also affected by other conditions, kind of specimen and other factors, it is possible to roughly infer that product ions with sufficient intensities for the structural analysis of the peptide will be observed when the laser spot size is equal to or smaller than 15 μm.

It can be inferred that, if the laser spot size is decreased to a smaller size than 5 μm, the plume 26 formed near the surface of the sample 23 will be even smaller, and its particle density will be even higher, so that the product ions due to the in-source decay will be more abundantly generated. However, it should be noted that there is a lower limit of the laser spot size for technical and cost-related reasons since the smallest possible size is restricted by the accuracy of the members constituting the device and their assembly accuracy. In practice, the lower limit of the laser spot size is considered to be approximately 1 μm or 2 μm.

Figure 5:
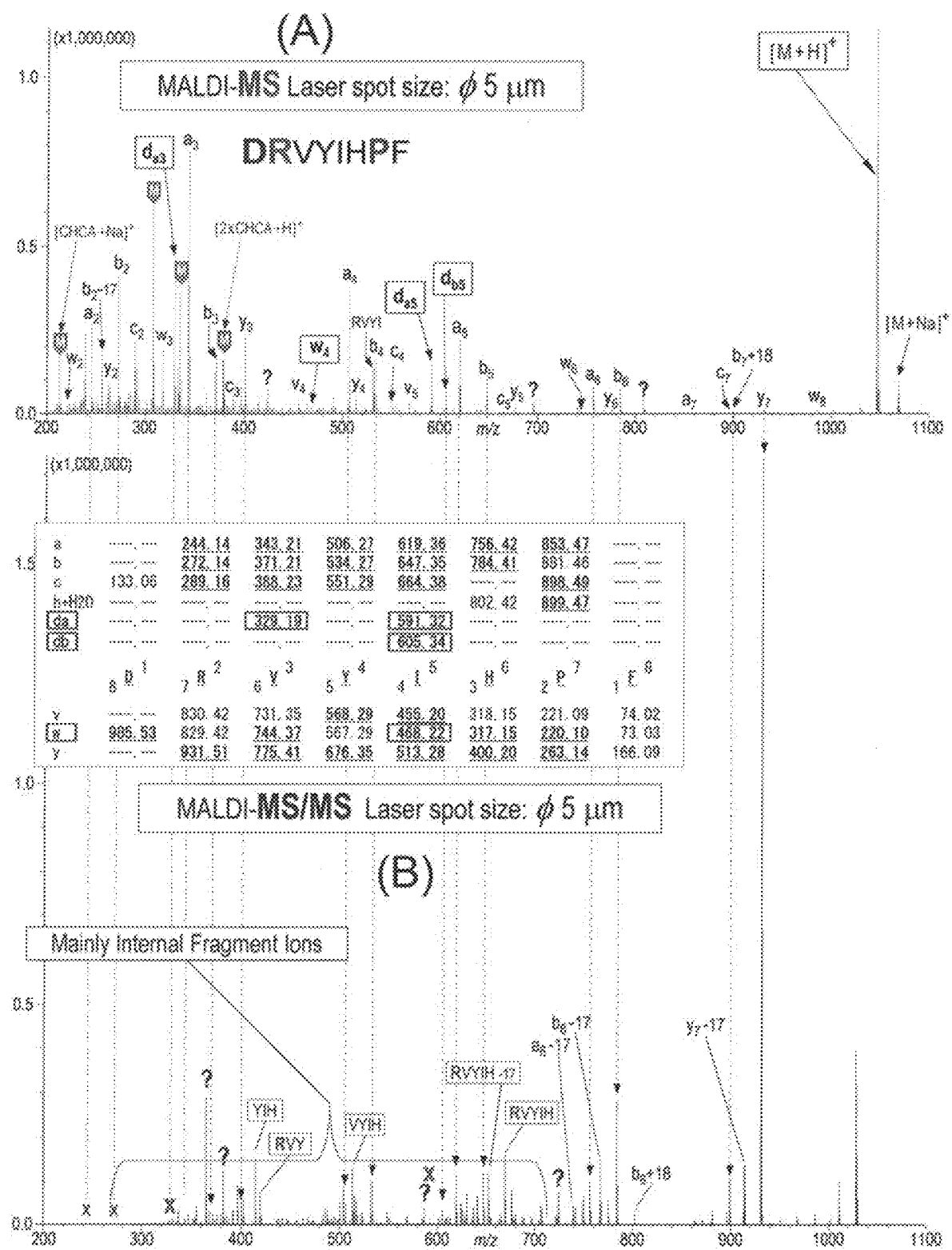
FIGS. 5A and 5B show an example of the comparison between an actual mass spectrum acquired by using in-source decay and one acquired by using an MS/MS analysis.

FIG. 5 at (A) and (B) shows an example of the comparison between an actual mass spectrum acquired by using in-source decay (FIG. 5 at (A)) and one acquired by using an MS/MS analysis (FIG. 5 at (B)) under the previously described analysis conditions of FIG. 4 at (A). The mass spectrum shown in FIG. 5 at (A) is the same as the one shown in FIG. 4 at (A).

The structure of the side chain of an amino acid significantly varies depending on the kind of amino acid. In particular, the amino acids which easily yield d-type ions are limited to specific kinds of amino acids, including leucine and isoleucine. The mass spectrum shown in FIG. 5 at (A) clearly shows the d$_{a5}$ ion at m/z 591.32 and d$_{b5}$ ion at m/z 605.34, both of which characterize the side chain of isoleucine. Isoleucine and leucine are identical in mass. However, in the case of leucine, d$_{a5}$ ion appears at m/z 577.31, and d$_{b5}$ ion does not appear at all. Accordingly, from the mass spectrum shown in FIG. 5 at (A), it can be understood that the fifth amino acid from the left end is isoleucine, not leucine.

Angiotensin II includes aspartic acid (symbol D) and proline (symbol P). If an MS/MS analysis using low-energy CID is performed for angiotensin II, the cleavage easily occurs at a bond on the right side of D and on the left side of P. Additionally, the desorption of NH$_3$ or H$_2$O often occurs. Therefore, as shown in FIG. 5 at (B), a comparatively large number of internal fragment ions resulting from complex fragmentation are observed, other than the a-type, b-type, c-type, y-type and other types of ions which retain the N-terminal or C-terminal. Those obstructive fragment ions make the structural analysis of the amino-acid sequence (or the like) difficult to perform. By comparison, those internal fragment ions are barely observed in the mass spectrum shown in FIG. 5 at (A). This also facilitates the structural analysis. Another advantage of the in-source decay over the MS/MS analysis exists in the higher efficiency of the analysis, which is due to the fact that the measurement time is shortened due to the omission of the process of capturing and dissociating ions by the ion trap. Still another advantage exists in that the analysis can be performed with a device that is inexpensive and readily obtainable (or already at hand), since in the first place it is unnecessary to use a device capable of an MS/MS analysis.

<Mixture Ratio of Specimen and Matrix>

Figure 6:
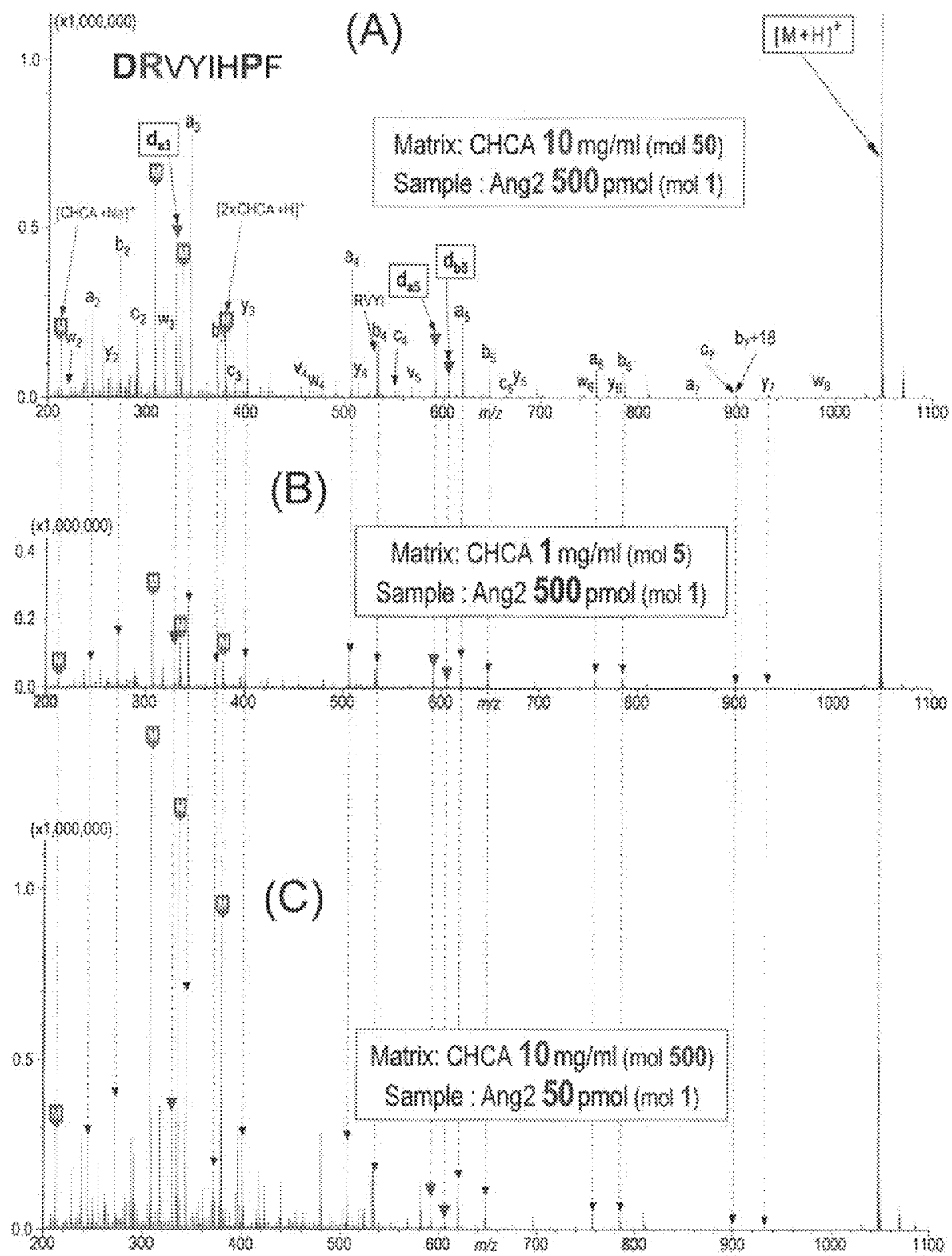
FIGS. 6A-6C show an example of the comparison of actual mass spectra acquired with different mixture ratios of the specimen and matrix.

FIG. 6 at (A)-(C) shows an example of the comparison of actual mass spectra acquired with different mixture ratios of the specimen and matrix. FIG. 6 at (A) is a mass spectrum acquired with the matrix and specimen mixed at a ratio of approximately 50:1 (in molar ratio). FIG. 6 at (B) is a mass spectrum acquired with the matrix and specimen mixed at a ratio of approximately 5:1 (in molar ratio). FIG. 6 at (C) is a mass spectrum acquired with the matrix and specimen mixed at a ratio of approximately 500:1 (in molar ratio).

The other analysis conditions were as follows:
Specimen: angiotensin II
Matrix: CHCA
Laser spot size: 5 μm
Sample plate: cover glass for microscope In a common type of MALDI method, the mixture ratio of the specimen and matrix in molar ratio is larger than 1:500, normally 1:10000 or even larger. However, a high ratio of the matrix means easier generation of the cluster ions originating from the matrix. In the case of observing the product ions of a peptide or similar organic compound having a comparatively small molecular weight, the important product ions appear within a mass-to-charge-ratio range from m/z 200 to a maximum of several thousands, while the cluster ions originating from the matrix also appear over the same mass-to-charge-ratio range. If there are a considerable number of cluster ions, it will be difficult to distinguish those cluster ions from the product ions of peptide origin. Accordingly, the specimen and matrix are mixed at a smaller ratio than in a common type of MALDI method to suppress the generation of the cluster ions originating from the matrix.

A comparison of the mass spectrum shown in FIG. 6 at (A) and the one shown in FIG. 6 at (B) demonstrates that there is no significant change in the generated ion species. Both mass spectra are also barely affected by the cluster ions originating from the matrix. However, the quantities of the ions of peptide origin in FIG. 6 at (B) are smaller than in FIG. 6 at (A). A likely reason for this is that the generation of the ions originating from the specimen decreased since the amount of matrix which promotes the ionization was significantly decreased as compared to the case of FIG. 6 at (A).

On the other hand, a comparison of the mass spectrum shown in FIG. 6 at (A) and the one shown in FIG. 6 at (C) demonstrates that there is no significant difference in the quantities of the detected ions of peptide origin, whereas the intensity of the cluster ions originating from the matrix is increased in FIG. 6 at (C). As in this example, increasing the amount of matrix relative to the amount of specimen causes a relative increase in the intensity of the ions originating from the matrix and the impurities contained in the matrix, which may possibly make the structural analysis difficult to perform. Those results suggest that, in order to acquire a mass spectrum that facilities the structural analysis, the mixture ratio of the matrix and specimen (in molar ratio) should be within a range from 5:1 to 5000:1, preferably equal to or lower than 1000:1, more preferably equal to or lower than 500:1, and even more preferably equal to or lower than approximately 50:1. It should be noted that those conditions can also vary depending on the other conditions, including the kind of matrix.

<Kind of Matrix>

FIG. 7 at (A)-(C) shows an example of the comparison of actual mass spectra acquired by using different kinds of matrices. It should be noted that the matrices tested in the measurement were not special ones, such as 1,5-DAN, but were readily obtainable, inexpensive, commonly used matrices. FIG. 7 at (A) is a mass spectrum acquired by using CHCA. FIG. 7 at (B) is a mass spectrum acquired by using DHB. FIG. 7 at (C) is a mass spectrum acquired by using sinapinic acid (SA). The other analysis conditions were as follows:
Specimen: angiotensin II
Mixture ratio of matrix and specimen: approximately 50:1 (in molar ratio)
Laser spot size: 5 μm
Sample plate: cover glass for microscope The mass spectrum shown in FIG. 7 at (A) is the same as the one shown in FIG. 4 at (A) and FIG. 5 at (A).

A comparison of the mass spectrum shown in FIG. 7 at (A) and the one shown in FIG. 7 at (B) demonstrates that, even in the case where DHB was used as the matrix, various product ions including the d-type ions were detected to the same degree as in the case where CHCA was used as the matrix. On the other hand, in the case where DHB was used, the cluster ions originating from the matrix were more abundantly observed than in the case where CHCA was used. Most of the mass-to-charge ratios of those cluster ions are equal to or smaller than m/z 800, and the mass-to-charge ratios at which the cluster ions will appear are roughly known beforehand. Therefore, those cluster ions are comparatively unobstructive, so that the structural analysis of the peptide can be performed.

In the mass spectrum shown in FIG. 7 at (C), the molecular ion of the peptide is almost unobservable, while the cluster ions originating from the matrix as well as its fragment ions are extremely large in quantity. SA is originally a matrix suited for the ionization of proteins or similar compounds having high molecular weights. This type of matrix is not suited for the ionization of peptides or similar compounds whose molecular weights are comparatively low.

From the result of this experiment, it is possible to conclude that CHCA produces the most satisfactory result among the commonly used matrices, while DHB is also usable. These are commonly used matrices for MALDI, which are readily obtainable and also help with cost reduction. Needless to say, the use of a special matrix other than the mentioned ones may also possibly provide sufficient molecular information.

From the viewpoint of the chemical or physical nature or the structural characteristics, a usable matrix should preferably satisfy the following conditions: the matrix should have an aromatic ring structure (particularly, benzene ring) as a main portion for absorbing ultraviolet laser light; the matrix should have a carboxyl group, for example, so that it can donate a proton or cation to the compound to be ionized; and the matrix should have a hydroxyl group, for example, for making the matrix soluble in a solvent (i.e., polar).

<Kind of Sample Plate>

FIG. 8 at (A)-(D) shows an example of the comparison of actual mass spectra acquired by using different kinds of sample plates. FIG. 8 at (A) is a mass spectrum acquired by using a cover glass as the sample plate. FIG. 8 at (B) is a mass spectrum acquired by using a slide glass as the sample plate. FIG. 8 at (C) is a mass spectrum acquired by using an ITO (indium tin oxide) glass as the sample plate. FIG. 8 at (D) is a mass spectrum acquired by using a stainless-steel plate as the sample plate. The other analysis conditions were as follows:

Specimen: angiotensin II
Matrix: CHCA
Mixture ratio of matrix and specimen: approximately 50:1 (in molar ratio)
Laser spot size: 5 μm Sample plates do not significantly affect the ionization of the components contained in the sample. However, the impurities adhered to the sample plate (stains, dust, etc.) as well as the components contained in the plate can cause chemical noise. A cover glass is a member that needs to be extremely clean and has a high level of surface flatness in order to enable a satisfactory observation through a microscope (or the like). Therefore, as is evident from FIG. 8 at (A), background noise is considerably reduced, particularly within a mass-to-charge-ratio range equal to or smaller than m/z 500. On the other hand, a slide glass is normally inferior to a cover glass in terms of cleanliness, so that background noise is higher to a certain extent, as shown in FIG. 8 at (B). However, this level of noise effectively poses no problem.

Glass is made of small elements, such as silicon, calcium and oxygen. Compounds of those elements (oxides) have comparatively high melting and boiling points. Therefore, even if the components constituting the glass are ionized, the resulting ions will pose little problem in normal cases since they will rarely appear within the important mass-to-charge-ratio range for an analysis of amino-acid sequence (m/z>200).

The ITO glass, which is frequently used for biological tissue observation in imaging mass spectrometry, is far more expensive than a cover glass or slide glass. Additionally, as shown in FIG. 8 at (C), ions of unknown origin (e.g., at m/z 417.85) with comparatively high levels of intensity appear within the mass-to-charge-ratio range of m/z>200. Those ions may possibly make the structural analysis of the peptide difficult to perform.

The stainless-steel plate has a rougher surface than a glass plate, and a stain is likely to be adhered to its surface. Although the background noise originating from impurities in the mass spectrum shown in FIG. 8 at (D) are comparatively low, it is difficult to control the plate so that no stain will be adhered to it.

The experimental results suggest that a cover glass or slide glass is a safe option for the sample plate, of which the cover glass can preferably be used.

There are also other ionization conditions, such as laser power, in addition to the previously described ones. Those conditions may be set at normal values used in MALDI mass spectrometers, or they may be appropriately adjusted according to common practice.

[Example of Application to Other Peptides]

The mass spectra shown in FIGS. 4-8 were all obtained for analyzing angiotensin II. As an example of the application of the method for structural analysis according to the present embodiment to other kinds of peptides, a mass spectrum acquired by a measurement of Glu-Fibrinopeptide B is shown in FIG. 9. As with FIG. 4 at (A) (or other figures), FIG. 9 includes a table showing the mass-to-charge ratios of various types of product ions which respectively correspond to the amino acids forming the target peptide, among which the ions detected on the mass spectrum shown in FIG. 9 are indicated by underlines and rectangular frames.

The analysis conditions were as follows:
Matrix: CHCA
Mixture ratio of matrix and specimen: approximately 50:1 (in molar ratio)
Laser spot size: 5 μm
Sample plate: cover glass for microscope Glu-Fibrinopeptide B is a peptide having arginine (symbol R) at its C-terminal. Arginine is likely to have a positive charge. Therefore, y-type ions are noticeably observed, rather than the a-, b- and c-type ions. On the other hand, the d-type and v-type ions which result from the cleavage of side chains are also abundantly observed. Cluster ions originating from the matrix (or the like) are barely observed. Therefore, it is possible to perform a satisfactory structural analysis based on the ion information of this mass spectrum.

This result demonstrates that the method for structural analysis according to the present embodiment is satisfactorily useful for not only angiotensin II but also other peptides.

The previous descriptions have been concerned with the cases of analyzing peptides. Proteins, which have longer peptide-bonded chains, can also be included in analysis targets. Furthermore, the present invention is also applicable to other kinds of organic compounds, such as glycans, lipids or nucleic-acid-related substances.

It should also be noted that the previous embodiment is a mere example of the present invention, and any change, modification, addition or the like appropriately made within the spirit of the present invention will naturally fall within the scope of claims of the present application.

Specifically, for example, the device for carrying out a mass spectrometric analysis in the present invention is not limited to a device configured as shown in FIGS. 2 and 3. Any device which fulfills the required conditions, including the ionization conditions, can be used. As a specific example, a quadrupole time-of-flight mass spectrometer including a MALDI ion source can be used.

It should be noted that structural analysis requires determining the mass-to-charge ratios of product ions with a considerably high level of accuracy. A preferable device from this viewpoint is a mass spectrometer employing a time-of-flight mass separator or other types of mass separators which are comparable with or superior to time-of-flight mass separators in terms of mass accuracy and mass-resolving power (e.g., Fourier-transform ion cyclotron resonance mass separator). The mass-to-charge-ratio range of the resulting mass spectrum depends on the method of mass separation (or other factors). Therefore, if the analysis target is a compound having a high molecular weight, it is preferable to select a mass spectrometer which yields a mass spectrum having the highest possible upper limit of the mass-to-charge ratio.

[Various Modes]

A person skilled in the art can understand that the previously described illustrative embodiment is a specific example of the following modes of the present invention.

(Clause 1) One mode of the present invention is a method for the structural analysis of an organic compound by matrix assisted laser desorption/ionization mass spectrometry, the method including:

a sample preparation process which includes preparing a sample by mixing a specimen containing an organic compound to be analyzed with a predetermined matrix at a mixture ratio within a range from 1:5 to 1:5000 in molar ratio;

a mass spectrometry process which includes irradiating the prepared sample with a laser beam having a spot size equal to or smaller than 15 µm to generate ions originating from a component of the specimen in the sample, and performing a mass spectrometric analysis of the generated ions; and an analyzing process which includes detecting, from a mass spectrum acquired in the mass spectrometry process, ions including product ions resulting from in-source decay, and estimating the structure of the organic compound to be analyzed based on information concerning the ions.

By the method for the structural analysis of an organic compound described in Clause 1, a mass spectrum on which useful product ions for a detailed structural analysis of a peptide, glycan, or similar organic compound are satisfactorily observed can be obtained without performing an MS/MS analysis using low-energy CID (or the like). Specifically, in the case where the organic compound to be analyzed is a peptide, not only ions resulting from the cleavage of the main chain of the peptide but also ions resulting from the cleavage of a side chain can be observed. Therefore, the time and labor for performing an MS/MS analysis can be omitted, so that a detailed structure of an organic compound, such as a peptide, can be efficiently understood with a high level of accuracy.

The method for the structural analysis of an organic compound described in Clause 1 can suppress cluster ions originating from the matrix occurring within a mass-to-charge-ratio range from m/z 200 to a maximum of several thousands, particularly at comparatively low mass-to-charge ratios within that range. Therefore, it is easy to detect product ions which originate from the target organic compound and should be observed within the aforementioned mass-to-charge-ratio range, so that the correctness of the structural analysis of the organic compound can be improved.

(Clause 2) In the method for the structural analysis of an organic compound described in Clause 1, the organic compound may be a peptide, protein or glycan.

(Clause 3) In the method for the structural analysis of an organic compound described in Clause 2, the organic compound may be a peptide, and the product ions may include both an ion resulting from cleavage of the main chain of the peptide and an ion resulting from cleavage of a side chain of the peptide.

By the method for the structural analysis of an organic compound described in Clause 3, the structure of the peptide including its amino-acid sequence can be correctly determined after discriminating between leucine and isoleucine which are two amino acids having the same mass.

(Clause 4) In the method for the structural analysis of an organic compound described in one of Clauses 1-3, the matrix may have a partial structure for absorbing ultraviolet laser light, a partial structure for donating a proton or cation, and a partial structure for making the matrix soluble in a solvent.

(Clause 5) In the method for the structural analysis of an organic compound described in Clause 4, the partial structure for absorbing ultraviolet laser light may be an aromatic ring, the partial structure for donating a proton or cation may be a carboxyl group, and the partial structure for making the matrix soluble in a solvent may be a hydroxyl group.

In particular, the aromatic ring may be a benzene ring.

(Clause 6) In the method for the structural analysis of an organic compound described in Clause 4 or 5, the matrix may be α-cyano-4-hydroxycinnamic acid (CHCA) or 2,5-dihydroxybenzoic acid (DHB).

By the method for the structural analysis of an organic compound described in one of Clauses 4-6, the product ions originating from an organic compound, such as a peptide, can be satisfactorily generated, while the generation of the cluster ions originating from the matrix and overlapping the product ions on a mass spectrum can be suppressed, so that a suitable mass spectrum for the structural analysis can be acquired. CHCA and DHB are commonly used matrices for a common type of MALDI method. Those matrices are readily obtainable as well as inexpensive and easy to handle for users.

(Clause 7) In the method for the structural analysis of an organic compound described in one of Clauses 1-6, a dried-droplet method or thin-layer method may be used for preparing the sample in the sample preparation process.

By the method for the structural analysis of an organic compound described in Clause 7, the in-source decay of an organic compound, such as a peptide, can be promoted, whereby a mass spectrum which facilitates the structural analysis can be acquired.

(Clause 8) In the method for the structural analysis of an organic compound described in one of Clauses 1-7, the sample may be prepared on a sample plate which is made of glass and has a smooth, clean surface in the sample preparation process.

By the method for the structural analysis of an organic compound described in Clause 8, a satisfactory mass spectrum can be obtained on which the product ions originating from the target organic compound can be satisfactorily observed while few ions originating impurities are present.

REFERENCE SIGNS LIST

1 . . . Measurement Unit
2 . . . Ionization Chamber
21 . . . Sample Stage
22 . . . Sample Plate
23 . . . Sample
24 . . . Laser Irradiator
241 . . . Ultraviolet Pulse Laser Source
242 . . . Variable Optical Filter
243 . . . First Lens of Beam Expander
244 . . . Second Lens of Beam Expander
245 . . . Objective Lens
3 . . . Vacuum Chamber
31 . . . Ion Transport Tube
32 . . . Ion Guide
33 . . . Ion Trap
34 . . . Time-of-Flight Mass Separator
35 . . . Ion Detector
4 . . . Data Processing Unit
5 . . . Analysis Control Unit
6 . . . Main Control Unit
7 . . . Input Unit
8 . . . Display Unit

The invention claimed is:

1. A method for a structural analysis of an organic compound by matrix assisted laser desorption/ionization mass spectrometry, the method comprising:
   a sample preparation process which includes preparing a sample by mixing a specimen containing an organic compound to be analyzed with a predetermined matrix at a mixture ratio within a range from 1:5 to 1:5000 in molar ratio;
   a mass spectrometry process which includes irradiating the prepared sample with a laser beam having a spot size equal to or smaller than 15 μm to generate ions originating from a component of the specimen the sample, and performing a mass spectrometric analysis of the generated ions; and
   an analyzing process which includes detecting, from a mass spectrum acquired in the mass spectrometry process, ions including product ions resulting from in-source decay, and estimating a structure of the organic compound to be analyzed based on information concerning the ions.

2. The method for a structural analysis of an organic compound according to claim 1, wherein the organic compound is a peptide, protein or glycan.

3. The method for a structural analysis of an organic compound according to claim 2, wherein the organic compound is a peptide, and the product ions include both an ion resulting from cleavage of a main chain of the peptide and an ion resulting from cleavage of a side chain of the peptide.

4. The method for a structural analysis of an organic compound according to claim 1, wherein the matrix has a partial structure for absorbing ultraviolet laser light, a partial structure for donating a proton or cation, and a partial structure for making the matrix soluble in a solvent.

5. The method for a structural analysis of an organic compound according to claim 4, wherein the partial structure for absorbing ultraviolet laser light is an aromatic ring, the partial structure for donating a proton or cation is a carboxyl group, and the partial structure for making the matrix soluble in a solvent is a hydroxyl group.

6. The method for a structural analysis of an organic compound according to claim 4, wherein the matrix is α-cyano-4-hydroxycinnamic acid or 2,5-dihydroxybenzoic acid.

7. The method for a structural analysis of an organic compound according to claim 1, wherein a dried-droplet method or thin-layer method is used for preparing the sample in the sample preparation process.

8. The method for a structural analysis of an organic compound according to claim 1, wherein the sample is prepared on a sample plate which is made of glass and has a smooth, clean surface in the sample preparation process.

* * * * *